United States Patent [19]
Kronberg

[11] Patent Number: 6,011,994
[45] Date of Patent: Jan. 4, 2000

[54] MULTIPURPOSE BIOMEDICAL PULSED SIGNAL GENERATOR

[75] Inventor: James W. Kronberg, Aiken, S.C.

[73] Assignee: Equitech Intl' Corporation, Aiken, S.C.

[21] Appl. No.: 09/159,978

[22] Filed: Sep. 24, 1998

Related U.S. Application Data

[60] Provisional application No. 60/059,880, Sep. 24, 1997.

[51] Int. Cl.[7] .................................................... A61N 1/08
[52] U.S. Cl. .............................................................. 607/66
[58] Field of Search .................................. 607/66, 69, 76, 607/72

[56] References Cited

U.S. PATENT DOCUMENTS

| | | | |
|---|---|---|---|
| 4,856,525 | 8/1989 | Van Den Honert | 607/66 |
| 4,895,154 | 1/1990 | Bartelt et al. | 607/66 |
| 5,217,009 | 6/1993 | Kronberg . | |
| 5,413,596 | 5/1995 | Kronberg . | |

OTHER PUBLICATIONS

R. B. Borgens, "New Horizons in the Treatment of Spinal Cord Injury," posted at http://www.vet/purdue.edu/cpr/main.html by the Center for Paralysis Research, School of Veterinary Medicine, Purdue University, printed Sep. 25, 1998.

R. E. Shupe, et al., "The Friendly Fields of RF," IEEE Spectrum, vol. 22, No. 6 (Jun., 1985), pp. 66–71.

J. D. Zoltan, "Electrical Stimulation of Bone: an Overview," Seminars in Orthopaedics, vol. 1, No. 4 (Dec., 1986), pp. 242–252.

*Primary Examiner*—Scott M. Getzow
*Attorney, Agent, or Firm*—Maria Reichmanis

[57] ABSTRACT

A pulsed signal generator for biomedical applications, including electrical stimulation of fracture healing, treatment of osteoporosis, or to strengthen a freshly-healed bone after a cast or other fixation device has been removed. The generator includes dual asymmetric oscillators and associated circuitry to deliver signals efficiently throughout the area to be treated. The components can readily be selected so as to produce any desired output signal, including fixed-magnitude signals and (via suitable voltage-regulating devices) variable-magnitude signals. In addition, the pulse frequency and/or interval can be fixed or adjustable, as may be convenient. In a preferred embodiment of the invention, the generator is powered by readily-available, inexpensive batteries.

22 Claims, 3 Drawing Sheets

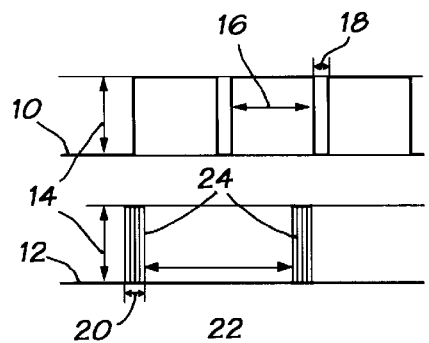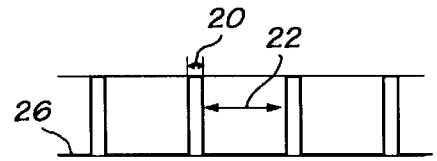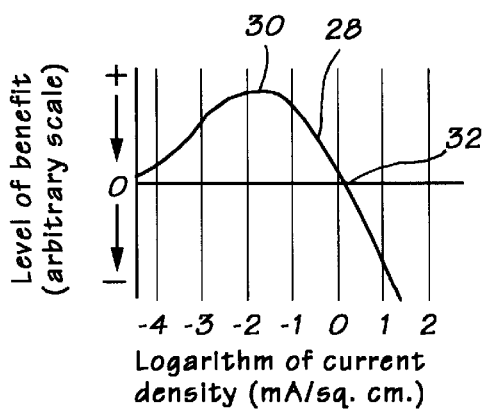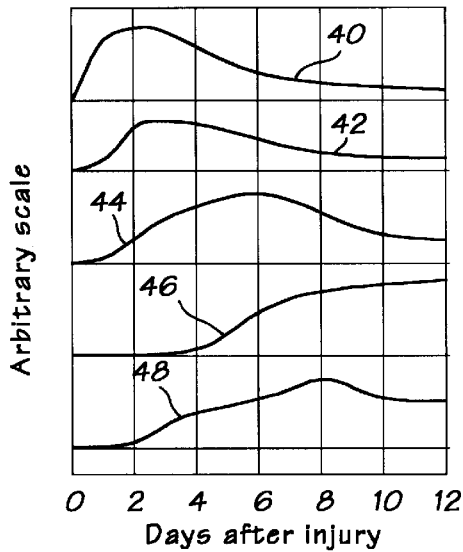
Fig. 1
Fig. 2
Fig. 3
Fig. 4
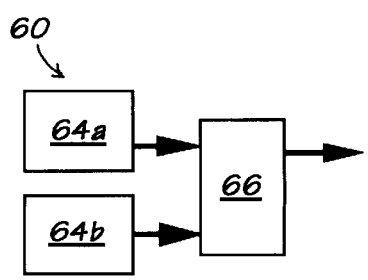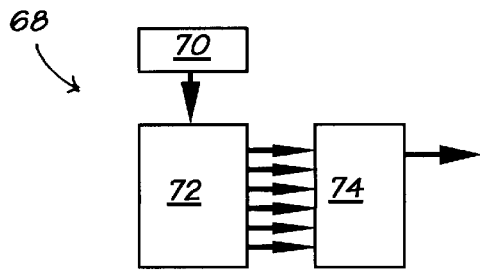
Fig. 5A
Fig. 5B

MULTIPURPOSE BIOMEDICAL PULSED SIGNAL GENERATOR

This application claims benefit of Provisional Application No. 60/059,880, filed Sep. 24, 1997.

BACKGROUND OF THE INVENTION

1. Field of the Invention

The present invention relates to a pulsed signal generator for biomedical applications. In particular, the present invention relates to a simple, compact pulsed signal generator for use in stimulation of fracture healing, treatment of osteoporosis, and other applications.

2. Discussion of Background

Several million Americans suffer broken bones every year; many of them having multiple fractures. Bone fractures are a major source of pain, inconvenience, expense, lost time and diminished workplace productivity. Even in a young, healthy patient, many fractures must be immobilized for six weeks or longer while healing takes place; after the cast or other fixation device is removed, the patient's activities must be restricted until the newly-healed bone regains its full strength. In the elderly population and in persons with poor health, malnutrition, or medical conditions such as diabetes that impact normal healing processes, fractures may heal slowly or not at all resulting in what are known as "nonunions."

Fracture healing, and in many cases the healing of other tissues as well, can be accelerated by the application of suitably-chosen, low-level electrical signals resembling those naturally present in tissues subjected to normal environmental levels of mechanical stress. Typical methods of doing this, however, require apparatus which is expensive, bulky and inconvenient to use, and/or requires surgical implantation.

Human bone is a combination of organic and mineral components. The chief mineral constituent of bone is hydroxyapatite, a complex calcium phosphate ($Ca_5(PO_4)_3OH$) in crystalline form. Like quartz, hydroxyapatite is piezoelectric: that is, it generates an electric charge or current when mechanically stressed. Collagen, the tough fibrous protein which surrounds the hydroxyapatite crystals and binds them together, is also piezoelectric.

Normally the electric signals generated by bone (sometimes called "bone talk") are weak and of relatively low frequency, replicating the pattern of mechanical forces placed on the bones from outside. When bone is strongly stressed, however, the hydroxyapatite crystals eventually start to slip little by little past each other and higher-frequency signals, having a characteristic pattern of sharp pulses separated by intervals of no signal, begin to appear. These signals arise from a mechanism much like that which creates the noise of a creaking floor: the wood surfaces or fibers alternately stick together and then, when the applied force becomes too great, give way abruptly and create a pulse of sound. Many such pulses in rapid succession make up the creaking sound we hear when walking across a creaking floor. A sensitive microphone can pick up the audio signals emitted by stressed bone; since any piezoelectric material is itself a microphone of sorts, the same pattern also appears as an electrical signal.

Osteoblasts, the cells within bone which secrete and deposit hydroxyapatite, are very sensitive to electric signals of this type and respond by forming larger amounts of hydroxyapatite. This creates a feedback mechanism, causing the bone to be strengthened automatically at points of stress concentration where the signals tend to be strongest. When the feedback loop breaks down-as when the bone receives little stress, when the diet is calcium-deficient, or when disease makes the cells less sensitive-osteoporosis can result. By the same token, restoring or strengthening the "bone talk" electrical signals can reverse or prevent the condition.

When a bone is fractured, current medical practice is first to "set" the bone with the fractured end surfaces close together, and then to immobilize it with a cast, splint, or fixator (internal or external) until the fracture heals. This practice has advantages and disadvantages. One advantage is that, since the fractured surfaces are close together, little bone tissue is needed to close the gap. On the other hand, the immobilized section of bone is exposed to little or no stress, next to no "bone talk" is generated, and thus, once again, the feedback loop which governs formation of new bone is broken. As a result, the osteoblasts in the vicinity of the fracture work at reduced capacity and the fracture takes a long time to heal. In all too many cases, complete healing never takes place and the fracture becomes a permanent nonunion.

It has long been known that the application of electric currents can restore healing (of nonunions) and speed bone growth and repair (of normal fractures). In the mid-1960s, C. A. L. Bassett and others measured the weak electrical signals generated by bone itself, analyzed and reproduced those signals artificially, and used them to reverse osteoporosis or aid in the healing of fractured bones.

A waveform which has been found effective is shown schematically in FIG. 1, where a line 10 represents the waveform on a short time scale, a line 12 represents the same waveform on a longer time scale, an interval 14 represents a peak voltage or current amplitude, and intervals 16, 18, 20, and 22 represent the timing between specific transitions. Alternate repetition of intervals 16 and 18 generates pulse bursts 24, each having a length 20 and separated by an interval 22 wherein the signal undergoes no transitions. For example, interval 16 may be about 200 microseconds, interval 18 about 28 microseconds, interval 20 about 5 milliseconds, and interval 22 about 62 milliseconds so that pulse bursts 24 recur at a frequency of about 15 Hertz.

The precise characteristics of the signal depicted in FIG. 1 are not at all critical. Indeed, the characteristics of naturally-occurring bone electrical signals depend on several factors, including the type, size and mineral density of the bone involved, the amount of stress and its rate of application, and probably on many other factors as well. Hence, osteoblasts are believed to be able to respond to a wide range of electrical signals. Typical laboratory studies of the effects of applied electrical signals on bone growth have been performed using signals that are approximately of the form shown in FIG. 1, with intervals 16, 18, 20 and 22 each within about a factor of five (i.e., from about 20% to about 500%) of the values given above. Some studies have utilized continuous pulse trains where interval 18 is reduced to zero. For example, a continuous pulse train 26 is shown in FIG. 2, may have an interval 20 of about 380 microseconds and an interval 22 of about 13 milliseconds, for a repetition rate of 75 Hertz (FIG. 2). Signals such as pulse train 26 have been used widely and successfully in treating osteoporosis.

While it was initially thought that signals applied from outside the body would have to be relatively strong to be biologically active, it now appears that a threshold effect is involved. Signals at levels comparable to those of normal "bone talk" (that is, resembling the signal shown in FIG. 1 with interval 14 representing a few microamperes per square centimeter of tissue cross-section) can increase the rate of healing in fresh fractures by as much as 100% and can restimulate healing in up to 80% of long-standing nonunions. Surprisingly, signals of like form but greater amplitude (as much as thousands of times more powerful) provide no greater benefit than the weaker signals, and often less. This relationship is shown in FIG. 3, where a line 28 represents the level of benefit at various signal intensities, where "benefit" refers to observable increases in healing (or normal fractures) or stimulation of healing (of nonunions). A peak applied voltage 30 typically falls somewhere around ten microamperes per square centimeter, and a crossover point 32 at about a hundred times this value. Beyond point 32, the signal slows healing rates rather than increasing them, and may itself cause further injury.

DC signals may also be useful, but are undesirable at almost any level since they can cause electrolytic damage to tissues through which they pass and, if too strong or of the wrong polarity, can actually cause bone loss.

Healing is a cellular process triggered by the occurrence of an injury (for purposes of this specification, the terms "wound" and "injury" refer to tissue damage or loss of any kind, including but not limited to cuts, incisions, abrasions, lacerations, fractures, contusions, burns, and so forth). In general, the progress of healing in any injured tissue, whether bone or a soft tissue such as skin or muscle, takes place in several well-defined stages of cell migration and proliferation. These are shown schematically in FIG. 4. Here, lines 40 through 44 represent the populations of various cell types involved in repair, while lines 46 and 48 show the progress of the repair through tissue rebuilding.

Neutrophils and monocytes, indicated by lines 40 and 42, respectively, are elements of the immune system which clean away damaged cells and destroy foreign organisms such as bacteria (if present) at the injury site. Their activity, which typically peaks from the second to the fourth day after the injury, corresponds to the inflammation phase of healing.

Fibroblasts, another type of cell indicated by line 44, then begin the repair process proper: building a framework of collagen, the same tough protein which binds the mineral components of bone together, and to which other cell types then adhere to form the rebuilt tissue. At about the same time, the number of capillaries, indicated by line 46, increases to supply needed materials for tissue rebuilding. The fibroblast population usually peaks around the sixth day after the injury, when the most rapid collagen formation is taking place (as shown by line 48). Once the basic framework is laid down, typically around the eighth day after the injury, the fibroblast population decreases. Collagen is deposited at a slower rate for several weeks more, while other types of cells continue to migrate into the injury site and proliferate to form a complete tissue.

Increases in the rate of healing have also been observed in soft-tissue injuries, such as nerve damage and skin wounds, when electrical signals were applied experimentally to the injured tissue or were being used to treat nearby bone. Hence, it seems likely that healing processes are naturally stimulated by "bone talk"-type electrical signals or by the piezoelectric response of other body tissues to environmental stress.

EXAMPLE

A volunteer patient was treated with a Bassett-type pulsed waveform in the spring of 1997. The patient had suffered three accidental abrasions on the dorsal surface of one hand; the abrasions were of approximately equal surface area. One abraded area (initially, slightly the worst of the three) was treated by application of a pulsed waveform of approximately 50 $\mu A/cm^2$; the second area was covered with electrode material but otherwise untreated; the third area was untreated. Results indicated that application of pulsed electrical stimulation roughly quadrupled the rates of the early healing stages compared to the covered and untreated areas. Inflammation in the treated abrasion was initially more severe than in the others; however, this phase of the healing process was completed much more quickly. After two days of intermittent treatment (two approximately 8-hour treatments on successive nights during sleep), the inflammation had almost completely subsided and a collagen framework for the new skin was already in place. This stage would normally not have been reached until about the eighth day post-injury.

Patients treated with the above-described types of pulsed signals often report quick relief from the pain accompanying fractured bones and traumatized soft tissues. The mechanism by which this occurs is likely the same one used in TENS (transcutaneous electric nerve stimulation), in which repeated electric pulses applied to a nerve, themselves so weak as to be imperceptible, can nevertheless block the transmission of pain signals to the brain. In the above-described example, the patient reported that sensation in the treated area had returned to essentially normal after approximately 48 hours of intermittent treatment.

Nerves respond to electrical stimuli not only by ceasing to transmit pain messages, but also, in at least some types of injury, by regenerating with increased speed. This effect has been demonstrated in a number of studies, including those conducted by Richard Borgens at the Purdue University School of Veterinary Medicine. Borgens reports that application of weak, oscillating electrical current across the site of an accidental spinal cord injury in a paraplegic dog can modify the growth and regeneration of damaged nerve fibers.

Electrical stimulation can also produce a wide range of responses in other body systems. The frequency and timing of the signal waveform appears to have some bearing on which of these are more affected. It appears possible that appropriately-designed waveforms may prove useful for stimulating muscles, such as those in fractured and immobilized limbs or those of temporarily paralyzed persons, to help prevent atrophy and preserve muscle tone. Other applications may include stimulation of the endocrine glands and the immune system. For example, autoimmune conditions such as arthritis may be susceptible to localized, bioelectric immunosuppression without affecting the ability of the body as a whole to throw off infection. Much more research will be needed in order to evaluate the potential of such effects in healing or in the treatment of diseases, and to determine the optimum waveform for each application.

Traditional Western medicine has accepted the efficacy of electrical stimulation only grudgingly, and despite its great healing potential it has so far been used only rarely. This may be a legacy from an early, widely-accepted hypothesis that electrical signals must have high intensities to be biologically effective, and that any effects are due solely to tissue heating. As a result, most presently-available devices rely either on direct implantation (of electrodes or of entire electronic packages) or on inductive coupling through the skin. The need for surgery and biocompatible materials in the one case, and excessive circuit complexity in the other, has kept the price of these devices very high, in the range of several thousands to tens of thousands of dollars each. Inductive coupling is also very inefficient, so that signals must originally be generated at hundreds or thousands of times the desired power level; hence the generators must either be plugged into a wall outlet during operation or require the user to carry around heavy, cumbersome battery packs. Only in the realm of TENS does it seem to have been widely realized that biologically effective signal levels can simply be transmitted through the skin, using self-adhesive electrodes, with minimal power loss.

Many different bone-growth stimulators are available, including those described in U.S. Pat. Nos. 5,217,009 and 5,413,596, the disclosures of which are incorporated herein by reference. The former design offers several advantages, including relatively low cost and light weight. However, it uses linear, analog timing integrated circuits with relatively high supply-current demand, requiring frequent battery changes while the device is in use.

The circuits of U.S. Pat. Nos. 5,217,009 and 5,413,596 are shown in block form in FIGS. 5A and 5B, as circuits 60 and 68, respectively. Circuit 60 includes two integrated timing circuits 64a, 64b and a logic section 66 (FIG. 5A). Circuit 68, described in U.S. Pat. No. 5,413,596, eliminates the timing circuits, but at the cost of much greater circuit complexity involving a clock oscillator 70 driving a binary divider chain 72 with multiple outputs to a logic section 74.

An ideal bioelectric signal generator for medical applications (including but not limited to bone repair or other healing applications) would be lightweight, compact, fully self-contained, inexpensive to build and maintain, safe for unsupervised home use by patients, and require no external coils or battery pack. The signal generator should be capable of being taped directly to an arm or leg cast, affixed to an athletic brace or external fixation device, fastened to a patient's arm or leg by VELCRO straps or other convenient means, or even simply be carried in the user's pocket, depending upon the condition to be treated and its location. Signals such as those described above, or alternatively signals of the same general form but with other timing characteristics, could be selected either by a suitable choice of components, or simply by turning a dial to select one of a plurality of available signals. Preferably, such a device would generate low-power, pulsed waveforms with high efficiency (and thus low battery drain) using only readily-available, low-cost circuit components, and without relying on linear, analog timing integrated circuits. Most preferably, such a device would be able to generate waveforms having a very wide achievable range of timing intervals so as to address a maximum possible range of applications, including bioelectronic therapy means requiring as-yet-unidentified waveforms.

SUMMARY OF THE INVENTION

According to its major aspects and broadly stated, the present invention is a portable, battery-powered pulsed signal generator. The generator, which is capable of generating the above-described "Bassett-type" waveforms, includes dual asymmetric oscillators and associated circuitry that, in combination, deliver a pulsed electrical signal efficiently throughout the area to be treated. The output signal of the generator is either fixed or variable, depending on the selection of components. The generator is light in weight, thus, it can be attached to a cast without any great increase in either weight or bulk. It is compact, self-contained, and can be taped to a cast, attached to an external fixation device, brace, or the like, or fastened to a patient's body by any convenient means. It can be used for a variety of biomedical applications, including stimulation of healing in nonunions, acceleration of normal healing, treatment of osteoporosis, or to strengthen a freshly-healed bone after a cast or other fixation device has been removed.

A major feature of the present invention is the use of asymmetric oscillator circuits to generate complementary waveforms that can be combined to produce an output waveform having virtually any desired characteristics. Surprisingly, the combination of a relatively simple asymmetrical resistive element or resistive network with a normally symmetrical oscillator circuit can create a circuit that generates a rectangular output signal whose characteristics—frequency, duty cycle, amplitude—can be determined over a wide range by the particular selection of components. Thus, two such circuits with complementary output signals can be combined to produce the desired output waveform.

An important feature of the present invention is the use of simple, inexpensive, readily-available components to produce the desired output signal, whether a "Bassett-type" signal or—by a suitable selection of components—some other biologically active signal that has a desired effect. Indeed, many of the components of the generator can be fabricated on a single logic chip, resulting in small size and cost-effective assembly.

Another feature of the present invention is the use of conventional, readily-available low-voltage batteries as a power source for the generator. This feature reduces the size and weight of the generator, and adds to its safety and ease of use for a patient undergoing treatment. Typically, the batteries need to be replaced at infrequent intervals (generally no more than once per week or even less often, depending on the output signal and the particular application), simplifying patient compliance and reducing cost. The possibility of electrical injuries is greatly reduced, since the generator is not connected to AC line current during use, does not produce high voltages, and does not generate frequencies likely to induce ventricular fibrillation. Because of the above-noted threshold effect, only low power levels are required to produce therapeutic effects; thus, the generator cannot produce an electrical shock hazard even in the event of a malfunction. Thus, the invention is suitable for unsupervised home use.

Still another feature of the present invention is its versatility. The components of the generator can readily be selected so as to produce any desired output waveform, including fixed-magnitude signals and (via suitable voltage-regulating devices) variable-magnitude signals. In addition, the pulse frequency, pulse interval, and (if desired) duty cycle can be fixed or adjustable, as may be convenient. It will be apparent that a generator having an adjustable output signal is useful for a variety of applications; on the other hand, medical professionals may prefer a generator having a fixed output, or an output that is adjustable only in magnitude, for outpatient use by their patients. In one embodiment of the invention, the user can select a signal for a given application by turning a dial or using a keypad to select one of a plurality of available signals. In another embodiment, the generator has complementary outputs (that is, the output waveform at one such output is equal to that at the other but of opposite polarity). Complementary outputs double the effective output voltage of the generator: a higher voltage not only yields greater flexibility in treatment options, but more easily permits a "swamping" resistor to be added in series with the output in order to minimize the effects of the resistance of intact skin.

Yet another feature of the present invention is the use of standard, readily-available TENS-type electrodes to deliver the biologically-effective signal. No special training is required to use these types of electrodes; prescribed treatment can be continuous, thereby minimizing problems related to patient compliance.

Other features and advantages of the present invention will be apparent to those skilled in the art from a careful reading of the Detailed Description of a Preferred Embodiment presented below and accompanied by the drawings.

BRIEF DESCRIPTION OF THE DRAWINGS

In the drawings,

FIG. 1 shows a waveform used for the stimulation of fracture healing;

FIG. 2 shows a waveform used for the treatment of osteoporosis;

FIG. 3 is a graph showing the attained benefit versus the logarithm of applied current density;

FIG. 4 illustrates the progression of healing in injured tissues;

FIGS. 5A and 5B are schematic views of two prior art signal generators;

DETAILED DESCRIPTION OF A PREFERRED EMBODIMENT

Figure 6:
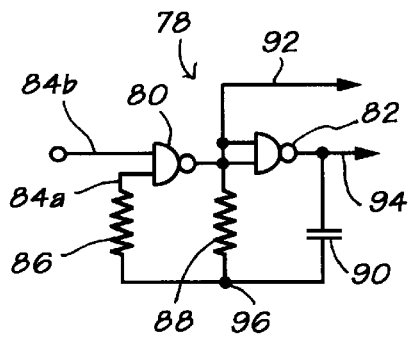
FIG. 6 is a circuit diagram of an oscillator circuit.

In the following detailed description, reference numerals are used to identify structural elements, portions of elements, surfaces and areas in the drawings. It should be understood that like reference numerals are intended to identify the same structural elements, portions or surfaces consistently throughout the several drawing figures, as such elements, portions or surfaces may be further described or explained by the entire written specification. As used in the following description, the terms "horizontal," "vertical," "left," "right," "up," "down," as well as adjectival and adverbial derivatives thereof (e.g., "horizontally," "rightwardly," "upwardly," etc.) refer to the relative orientation of the illustrated structure as the particular drawing figure faces the reader. Similarly, the terms "inwardly" and "outwardly" refer to the orientation of a surface of revolution relative to its axis.

Referring now to FIG. 6, there is shown an oscillator circuit 78 that is widely used as a clock in CMOS (i.e., complementary metal oxide semiconductor) circuits where frequency accuracies of a few percent (plus or minus) are deemed acceptable. Circuit 78 includes gates 80 and 82, which may be either simple inverters, gates of other types "left over" in circuit packages and with inputs tied together or to appropriate logic levels so that they function as inverters, or, optionally, such gates with the additional inputs used to permit on-off control. For example, gate 80 is shown in FIG. 6 as a two-input NAND gate with one input 84a functioning in the oscillator and the other input 84b providing control, such that the oscillator runs only when this input is at a positive logic level. Similarly, gate 82 is also shown as a two-input NAND gate but with both inputs tied together so that the gate functions as a simple inverter.

The output 92 of gate 80 is connected to the inputs of gate 82, while resistors 86, 88 and a capacitor 90, respectively, connect input 84a, output 92, and output 94 of gate 82 to a circuit node 96 which is otherwise isolated.

Figure 7:
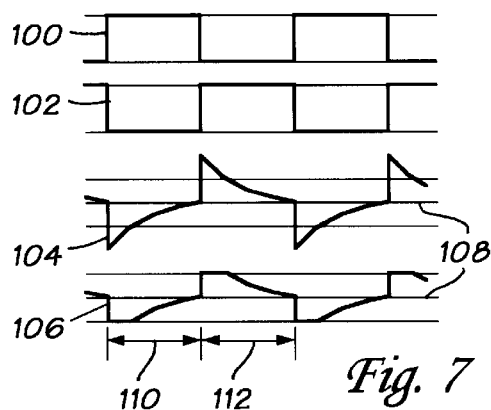
FIG. 7 illustrates the operation of the oscillator of FIG. 6.

The operation of oscillator circuit 68 is illustrated in FIG. 7. Lines 100, 102, 104 and 106 represent the voltages at output 92, output 94, node 96, and input 84a, respectively, as functions of time. Outputs 92 and 94 are complementary.

An upward transition of output 92 (shown as a voltage 100) causes an immediate downward transition in output 94 (shown as a voltage 102) which is relayed through capacitor 90 to node 96, causing a voltage 104 of node 96 to be lowered by a like amount. Since resistor 88 ties node 96 to output 92, which is now "high," voltage 104 then increases gradually, with a time constant determined chiefly by the product of resistor 88 and capacitor 90, toward the positive logic level.

A voltage 108, set approximately midway between the positive and negative supply levels (which for CMOS logic, approximately equal the logic output levels), represents the level of input 84a (a voltage 106) at which output 92 changes state. The exact value of voltage 108 depends on the specific type of device and manufacturing technology; however, the value of voltage 108 is reasonably consistent among devices of the same general type number (for example, CD4001B quad NAND gate ICs (integrated circuits)) from the same manufacturer.

Voltage 106 is approximately equal to voltage 104 as long as voltage 104 is between the positive and negative supply levels; however, voltage 106 is typically clipped above and below these levels by protective diodes within gate 90. Resistor 86 prevents this clipping action from drawing excessive current from node 96. Resistor 86 preferably has a value at least twice, and more preferably between five and ten times, the value of resistor 88.

The time needed for voltage 104 to decay from its initial value to a voltage 108 is shown in FIG. 7 as an interval 110. Provided that resistor 86 is sufficiently larger than resistor 88, interval 110 closely approximates the product of resistor 88 and capacitor 90 times the natural logarithm of 3, or approximately 1.10. By way of example, for values of 10,000 Ω for resistor 88 and 0.1 μf for capacitor 90, interval 110 is approximately 1.1 msec.

At the instant when voltage 106 first rises above voltage 108 (and provided that input 84b in FIG. 6, or equivalent inputs in other arrangements, is in the appropriate logic state to permit this action), gate 80 changes state and output 92 abruptly comes "low"; output 94 immediately goes "high," capacitor 90 relays the change to node 96, and voltages 104 and 106 are driven "high." The same voltage-decay process then takes place through resistor 88 as before, but in reverse since output 92 is now "low." Again, the time required is about 1.10 times the product of resistor 88 and capacitor 90. Hence, intervals 110 and 112 are equal (or approximately so) and the output is, at least to a close approximation, a square wave.

While the circuit of FIG. 6 is used in this way, it has not heretofore been recognized that intervals 110 and 112 can be made unequal, resulting in an output that is an approximately rectangular wave having essentially any desired duty cycle. Surprisingly, this result can be obtained simply by replacing resistor 88 with an asymmetrical resistive element or network.

A suitable resistive network may be formed by adding another resistor 120 in series with resistor 88 and shunting resistor 120 with a diode 122. In this arrangement, current flowing from node 96 toward output 92 "sees" only resistor 88 plus a slight voltage drop in the forward-biased diode, while current flowing from output 92 toward node 96 sees both resistors in series since diode 122 is now reverse-biased. Hence, in the corresponding voltage curves shown in FIG. 9, interval 110 is significantly longer than interval 112. Nearly any desired duty cycle can be attained simply by choosing the correct ratio between the two resistors 88 and 120. Similarly, reversing the direction of diode 122 makes interval 112 correspondingly longer than interval 110.

Additional network arrangements utilizing the above-described principle are also possible within the spirit of the present invention. As one of many possible examples, resistor 88 can be connected directly between node 96 and output 92 as shown in FIG. 6, but with the series combination of resistor 120 and diode 122 in parallel with resistor 88 so that one current polarity "sees" resistor 88 alone while the other "sees" resistors 88 and 120 in parallel.

Such an asymmetric oscillator, by itself, can generate a continuous pulse train like that shown in FIG. 2. To generate an intermittent waveform of pulse bursts alternating with "quiet" periods, like the classic "Bassett-type" waveform shown in FIG. 1, requires a cascade or other logical interconnection between two such oscillators: either with the outputs of both combined by external logic (analogous to block diagram 60 in FIG. 5) or, preferably, with the lower-frequency oscillator running continuously but switching on the higher-frequency one only when it is needed. Such an arrangement is described below.

Figure 8:
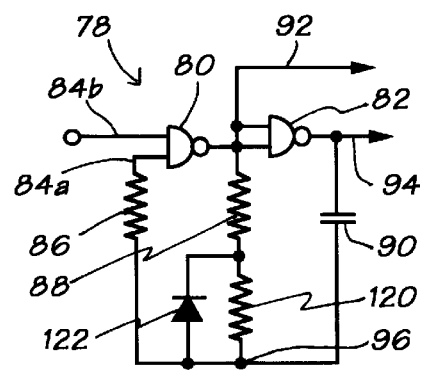
FIG. 8 is a circuit diagram of an oscillator circuit according to a preferred embodiment of the present invention.
Figure 10:
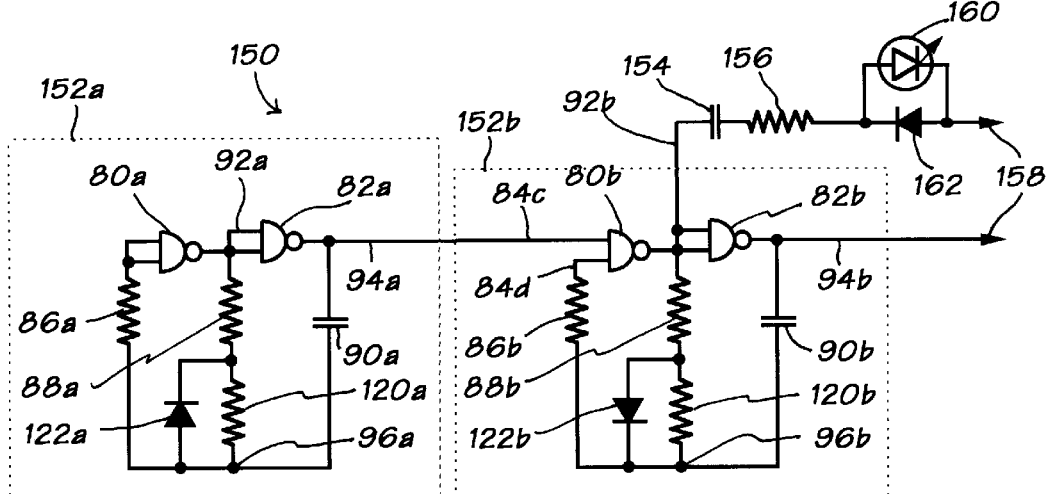
FIG. 10 is a circuit diagram of a signal generator according to a preferred embodiment of the present invention.

Referring now to FIG. 10, there is shown a signal generator 150 according to a preferred embodiment of the present invention. Generator 150 includes two oscillator sections 152a, 152b. For clarity, some of the components of generator 150 are given the same reference characters as appear in the circuit of FIG. 8, however, the suffix "a" or "b" is appended to differentiate components of the two oscillators 152a, 152b. An exception to this rule is made for the inputs to gates 80a and 80b, as will be explained further below.

Figure 9:
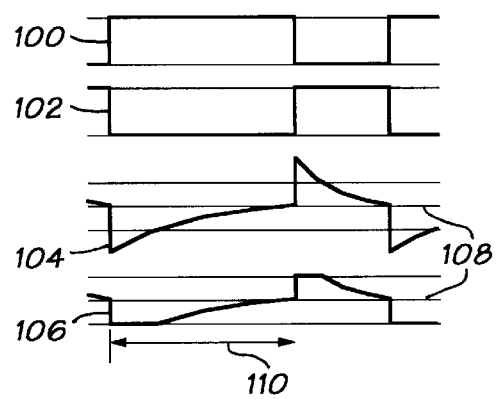
FIG. 9 illustrates the operation of the oscillator of FIG. 8.

Oscillator section 152a produces a waveform at output 94a consisting of alternating logic "low" and logic "high" periods corresponding respectively to intervals 110 and 102 in FIG. 9. Interval 110 further corresponds to interval 22 in FIG. 1 while interval 112 corresponds to interval 20. Output 94 is thus alternately "high" for about five msec, and "low" for about 62 msec. By way of example, an output 94 with these properties may be achieved by selecting a capacitor 90a of about 0.1 µf, a resistor 88a of about 43,000 Ω, a resistor 120a of about 510,000 Ω and a resistor 86a of any convenient value from about 2.2 MΩ up. Of course, other values for these components may also be useful for the practice of the invention. Because of normal type-to-type and manufacturer-to-manufacturer variations in gate threshold voltage 108, the optimum values of these components are determined by a modest amount of experimentation and observation for each particular application and type of component.

In oscillator 152a, gate 80a acts as a simple inverter with its input(s) driven solely by the voltage relayed through resistor 86a from node 96a. Output 92a from this gate is used only to drive the input(s) of gate 82a and the network of resistors 88a and 120a and diode 122a, and does not leave block 152a.

Output 94a, with the characteristics already described, leaves block 152a and passes into block 152b, where it is applied to input 84c of gate 80b to provide on-off switching of gate 80b. When input 84c is low, output 92b is always "high," output 94b is always "low," and no oscillation takes place. Node 96b rapidly takes on the same voltage as output 92b; once this occurs, the current drawn by the oscillator block is in the range of a few nanoamperes. When input 84c is "high," however, gate 80 acts as an inverter driven by input 84d and block 152b oscillates in the manner previously described, producing complementary signals on outputs 92b and 94b.

Since the desired output during interval 20 (as measured at output 92b) consists of a series of positive pulses which are relatively longer than the intervals between them, while the desired output during interval 22 is negative, diode 122b preferably has an orientation opposite that of diode 122a. This permits oscillator block 152b to generate a negative interval 18 which is shorter, by any desired ratio, than positive interval 16. For the preferred "Bassett-type" pulse intervals of 28 µsec and 200 µsec, respectively, capacitor 90b may have a value of approximately 0.001 µf, resistors 88b and 120b values of about 22,000 and 150,000 Ω each, and resistor 86b any convenient value from about 680,000 Ω up. For example, resistors 86a and 86b may have equal values e.g. of 2.2 MΩ each. Because of normal type-to-type and manufacturer-to-manufacturer variations in gate threshold voltage, the optimum values of these components are determined by a modest amount of experimentation and observation for each particular application and type of component.

Outputs 92b and 94b are complementary, so the AC components of the voltage measured between them will be twice those of either output alone. Capacitor 154 blocks all DC components of the signal, and resistor 156 helps to minimize the effects of skin resistance, so that the final output signal which appears between output terminals 158 is appropriately current-limited, contains no net DC, and consists either of the classic "Bassett" waveform or of another waveform selected for the particular application in view. If a visual indication of output is desired, a light-emitting diode 160 or other suitable device may be placed in series with the output as well. Since LED 160 blocks the reverse flow of current, a signal diode 162 is preferably set antiparallel to LED 160 to furnish a path for this current. It may be noted here that capacitor 154, resistor 156, and the antiparallel combination of diodes 160 and 162 (if used) may be placed indifferently in series with either output 92b, 94b, or distributed in any fashion between these lines, as may be most convenient.

Alternatively, resistor 156 may be replaced with a potentiometer (not shown) so that the user can regulate the amplitude of the output current. This ability is particularly useful for applications such as TENS, where the signal amplitude is preferably set as high as possible without its being directly perceptible to the user. For muscle stimulation, an even higher setting may be desirable, since an electrically-induced muscle twitch will almost certainly be noticed by the user but too-strong twitches are perceived as being annoying. Furthermore, individual thresholds for sensation, discomfort, and outright pain vary widely. Therefore, a device with a potentiometer, or other adjustable amplitude-controlling means, allows the user to set a stimulation level which strikes a balance between comfort and effectiveness.

Yet another modification to the output side of circuit 150 is accomplished by replacing resistor 156 with the primary winding of a small audio transformer (not shown) of the sort commonly found in transistor radios. This permits the output voltage to be stepped either up or down, as might best suit the specific requirements of the application.

Figure 11:
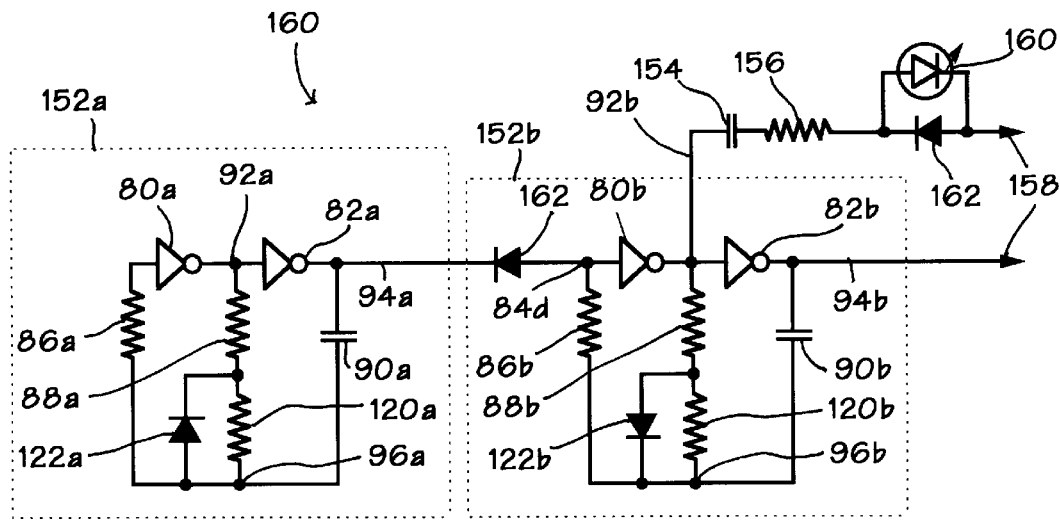
FIGS. 11 and 12 are circuit diagrams of additional signal generators according to the invention.

Another embodiment 160 of the present invention, shown in FIG. 11, differs from the embodiment of FIG. 10 chiefly in that logic gates 80a, 82a, 80b and 82b are simple inverters. This permits the use of relatively high-current-capacity logic buffers or data-line drivers such as those in the CD4049UB or CD4069UB hex inverter packages. Switching of high-frequency oscillator block 152b is accomplished by placing a single additional diode 162 between output 94a and input 84d. With output 94a "low," input 84d is held at logic "low" regardless of the voltage at node 96b. Because output 92b is "high," some small current flows through the series combination of resistors 86b, 88b and 120b and thus it is advantageous to make resistor 86b, at least, as large as possible.

Further power reduction can be achieved by giving capacitors 90a and 90b values as small as practical. In general, however, values less than approximately 100 pf are less useful since the gates' effective input capacitances may vary by a significant fraction of this amount due to nonlinear space-charge effects in the semiconductor material. In addition, resistance values are preferably less than approximately 10 MΩ due to the possibility of interference by current leakage in the reverse direction through resistor 162 for higher resistances, or, especially in humid weather, over the surfaces of the various circuit components.

Practical ranges of values for the resistors and capacitors in circuit 160 are the same as for circuit 150, therefore, save that, if practical, the resistance of resistor 86b should be in the range between approximately 2.2 MΩ and 10 MΩ, inclusive.

Figure 12:
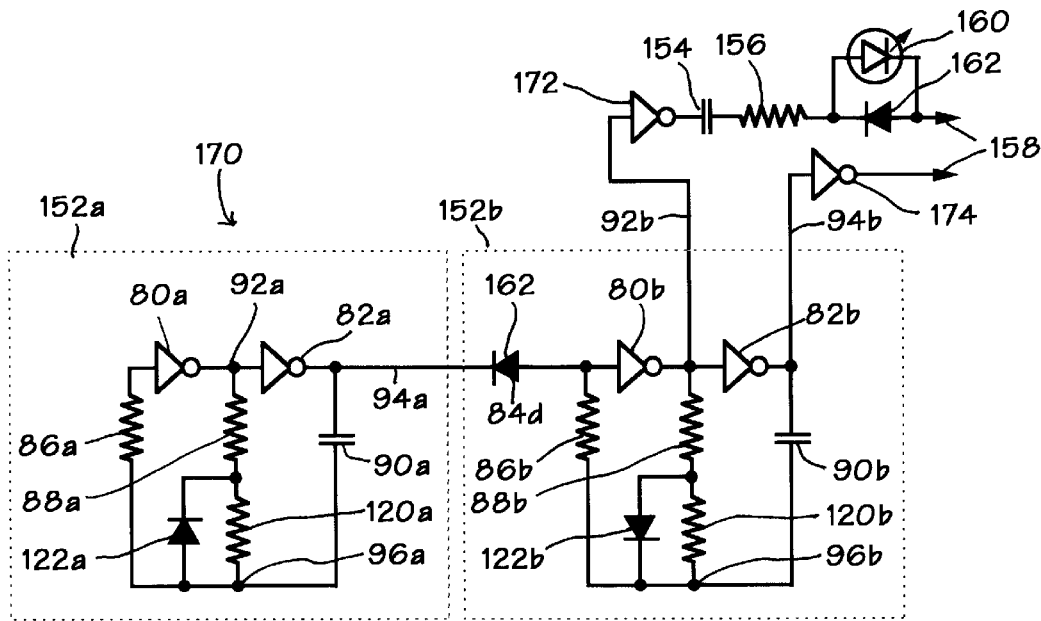

An advantage of using integrated-circuit packages such as the CD4049UB or CD4069UB is that, since there are six inverters in such a package, two of the inverters may be used to buffer the outputs and thus isolate the internal, timekeeping portions of the circuit from possible interference from outside electrical noise or changes in loading. This is shown in the circuit of FIG. 12, where gates 172 and 174 serve as the output buffers and are driven by outputs 92b and 94b, respectively. As before, capacitor 154 and resistor 156 are placed in either output line—in this case, either that following buffer 172 or that following buffer 174—to remove the DC component from the output signal and lessen the effect of skin resistance. LED 160 and diode 162 may also be added if a visual confirmation of output is desired. Also as before, the arrangement and distribution of these components between two output lines, leading to output terminals 158, is of no practical consequence.

In any of the specific embodiments described above, terminals 158 are preferably designed to accept flexible cables leading to electrodes (not shown) which make contact with the tissues to be treated, or to adjacent skin areas. These may be TENS-type, self-adhesive skin electrodes, although other electrode types may be useful for some applications.

Additional components may be added to the above-described signal generator without departing from the spirit of the present invention. Audible or tactile indicators may be useful to some persons (it should be noted that LED 160 functions as a visible "on-off" and low-battery indicator). The output waveform may be monitored by any convenient means, with an associated warning signal to alert the user when the waveform characteristics (frequency, pulse interval, magnitude, etc.) deviate from the selected characteristics by some predetermined amount. Such a warning signal could be used, for example, to alert the user to the need to change the batteries that power the generator. While DC power supplied by batteries is preferred, the generator may, if desired, include an AC adapter so that it can be operated by line current.

As noted above, a pulsed signal generator according to the present invention may have an adjustable output waveform; however, medical professionals may prefer a generator having a fixed output, or an output that is adjustable only in magnitude, for outpatient use. It will be apparent that the output waveform can be adjusted by any of a variety of techniques. By way of example, the generator may include any or all of the following: a potentiometer for adjusting the output amplitude; a switch for adjusting the polarity; a dial or keypad for selecting one of a plurality of available outputs; individual controls for adjusting the output pulse frequency, duration, and duty cycle. If desired, the generator may include a user-programmable microprocessor for adjusting any or all of these signal characteristics.

In one embodiment of the present invention, the generator has complementary outputs (that is, the output waveform at one of the outputs is approximately equal to that at the other but of opposite polarity). Complementary outputs double the effective output voltage of the generator: a higher voltage not only yields greater flexibility in treatment options, but more easily permits a "swamping" resistor to be added in series with the output in order to minimize the effects of the resistance of intact skin.

A pulsed signal generator according to the present invention makes use of simple, readily-available, generally inexpensive components to provide a rugged, reliable unit that may be tailored for a variety of biomedical applications. As will now be evident, the components of the generator can be selected to provide a device having an adjustable output (that is, adjustable in magnitude, polarity, frequency, or any combination of these factors), or a device that is specifically geared to a particular application, including but not limited to stimulation of fracture healing, TENS, osteoporosis treatment, etc.

With respect to the above description of the invention, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing description is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention. Thus, it will be apparent to those skilled in the art that many changes and substitutions can be made to the preferred embodiment herein described without departing from the spirit and scope of the present invention as defined by the appended claims.

What is claimed is:

1. A device for generating a pulsed electrical signal for use in biomedical applications, said device comprising:

first means for producing asymmetric oscillations, said first oscillator means producing a logic signal having first oscillations when said device is in electrical connection with a power source;

second means for producing asymmetric oscillations, said second oscillator means producing second oscillations when said device is in electrical connection with a power source, said second oscillations being complementary to said first oscillations;

circuit means for combining said first and second oscillations to produce an output waveform, said circuit means operating to switch said second oscillator "on" or "off" depending on a state of said logic signal; and output means for transmitting said output waveform to electrodes for stimulating biological tissue.

2. The device as recited in claim 1, wherein said first oscillator means further comprises means for generating a first series of electrical pulses, each pulse of said first series having a first amplitude, a first width, and a first frequency.

3. The device as recited in claim 1, wherein said second oscillator means further comprises means for generating a second series of electrical pulses, each pulse of said second series having a second amplitude, a second width, and a second frequency.

4. The device as recited in claim 1, further comprising indicator means in electrical connection with said output means, said indicator means providing an indication of an operational state of said device.

5. The device as recited in claim 1, further comprising means for adjusting a magnitude of said output waveform, said magnitude-adjusting means electrically connected to said output means.

6. The device as recited in claim 1, further comprising means for adjusting a polarity of said output waveform, said polarity-adjusting means electrically connected to said output means.

7. The device as recited in claim 1, further comprising means for adjusting a frequency of said output waveform, said frequency-adjusting means electrically connected to said output means.

8. The device as recited in claim 1, wherein said output waveform is a pulse train having a pulse interval, further comprising means for adjusting said pulse interval, said interval-adjusting means electrically connected to said output means.

9. The device as recited in claim 1, wherein said output waveform has preselected characteristics, further comprising means in electrical connection with said output means for monitoring said output waveform, said monitoring means providing a warning signal if said output waveform deviates from said preselected characteristics.

10. The device as recited in claim 1, wherein at least one of said first and said second oscillator means further comprises:

first signal-inverting means;

second signal-inverting means, said second signal-inverting means having an input driven by an output of said first signal-inverting means;

asymmetric resistive means coupling said output of said first signal-inverting means to a signal node;

capacitor means coupling an output of said second signal-inverting means to said signal node; and resistor means coupling said signal node to an input of said first signal-inverting means.

11. The device as recited in claim 1, wherein said second frequency is higher than said first frequency.

12. A device for generating a pulsed electrical signal for use in biomedical applications, said device comprising:

a first asymmetric oscillator, said first oscillator producing a first output signal when said device is in electrical connection with a power source;

a second asymmetric oscillator, said second oscillator producing a second output signal when said device is in electrical connection with said power source, said second output signal being complementary to said first output signal, at least one of said first and second oscillators including a first signal inverter having an output, a second signal inverter having an input driven by said output of said first signal inverter, an asymmetric resistive circuit coupling said output of said first signal inverter to an isolated signal node, at least one capacitor coupling an output of said second signal inverter to said isolated signal node, and at least one resistor coupling said isolated signal node to an input of said first signal inverter;

means for combining said first and second output signals to produce an output waveform; and means for transmitting said output waveform to electrodes for stimulating biological tissue.

13. The device as recited in claim 12, wherein at least one of said first and said second signal inverters is a CMOS logic gate.

14. The device as recited in claim 12, wherein at least one of said first and said second signal inverters includes means for controlling operation of a selected oscillator of said first and said second oscillators.

15. The device as recited in claim 12, wherein said at least one of said first and said second signal inverters is selected from the group consisting of multiple-logic gates, multiple-logic networks, simple inverters, NAND devices, and NOR devices.

16. The device as recited in claim 12, wherein said output of said first oscillator is a logic signal, said logic signal being applied to an input of at least one of said first and said second signal inverters, said logic signal acting to switch said second oscillator "on" or "off" depending upon a state of said logic signal.

17. The device as recited in claim 12, wherein said asymmetric resistive circuit further comprises at least one resistor and at least one diode.

18. The device as recited in claim 12, wherein said asymmetric resistive circuit further comprises:

a first resistor;

a second resistor connected in series with said first resistor; and a diode shunting a selected resistor of said first and said second resistors.

19. The device as recited in claim 12, wherein said asymmetric resistive circuit further comprises:

a first resistor;

a diode connected in series with said first resistor to form a series circuit; and a second resistor connected in parallel with said series circuit.

20. The device as recited in claim 12, further comprising means for adjusting a selected characteristic of said output waveform, said adjusting means including at least one component selected from the group consisting of adjustable components and switchable components.

21. The device as recited in claim 12, further comprising indicator means in electrical connection with said output means, said indicator means providing an indication of an operational state of said device, said indicator means being selected from the group consisting of optical indicators, audible indicators, and tactile indicators.

22. The device as recited in claim 12, wherein said first output signal has a first frequency, and wherein said second output signal has a second frequency higher than said first frequency.

* * * * *